United States Patent [19]

Wiita et al.

[11] Patent Number: 5,313,934
[45] Date of Patent: May 24, 1994

[54] LENS CLEANING MEANS FOR INVASIVE VIEWING MEDICAL INSTRUMENTS

[75] Inventors: Bruce E. Wiita, North Palm Beach; J. Michael Teets, Hobe Sound; Gregory D. Wiita, Palm Beach Gardens, all of Fla.

[73] Assignee: Deumed Group Inc., Palm Beach Gardens, Fla.

[21] Appl. No.: 943,315

[22] Filed: Sep. 10, 1992

[51] Int. Cl.$^5$ ............................................. A61B 1/00
[52] U.S. Cl. ........................................ 128/4; 128/6; 128/7
[58] Field of Search ................................. 128/4, 6, 7

[56] References Cited

U.S. PATENT DOCUMENTS

| 4,770,163 | 9/1988 | Ono et al. | 128/6 |
| 4,878,485 | 11/1989 | Adair | 128/4 X |
| 4,934,786 | 6/1990 | Krauter | 128/4 X |
| 4,959,058 | 9/1990 | Michelson | 128/4 X |

FOREIGN PATENT DOCUMENTS

| PK6140 | 5/1991 | Australia | 128/6 |
| 9220274 | 11/1992 | PCT Int'l Appl. | 128/6 |

Primary Examiner—Richard J. Apley
Assistant Examiner—Beverly A. Meindl
Attorney, Agent, or Firm—Norman Friedland

[57] ABSTRACT

A hollow tubular elongated member is concentrically mounted to a borescope or surgical viewing instrument defining a spaced passage for flowing fluid to a cuff which is discretely located below the distal end of the lens of the borescope and which defines a discretely configured discharge port for flowing fluid over the lens surface for cleansing and defogging purposes. A two-piece locking handle may be used to lock the lens cleaning apparatus to the borescope. Another embodiment includes a flexible tube utilized with the cuff.

12 Claims, 6 Drawing Sheets

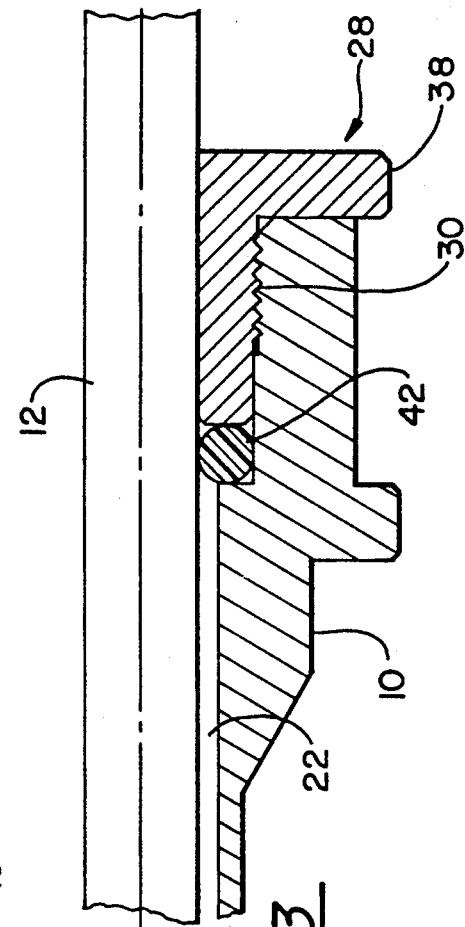
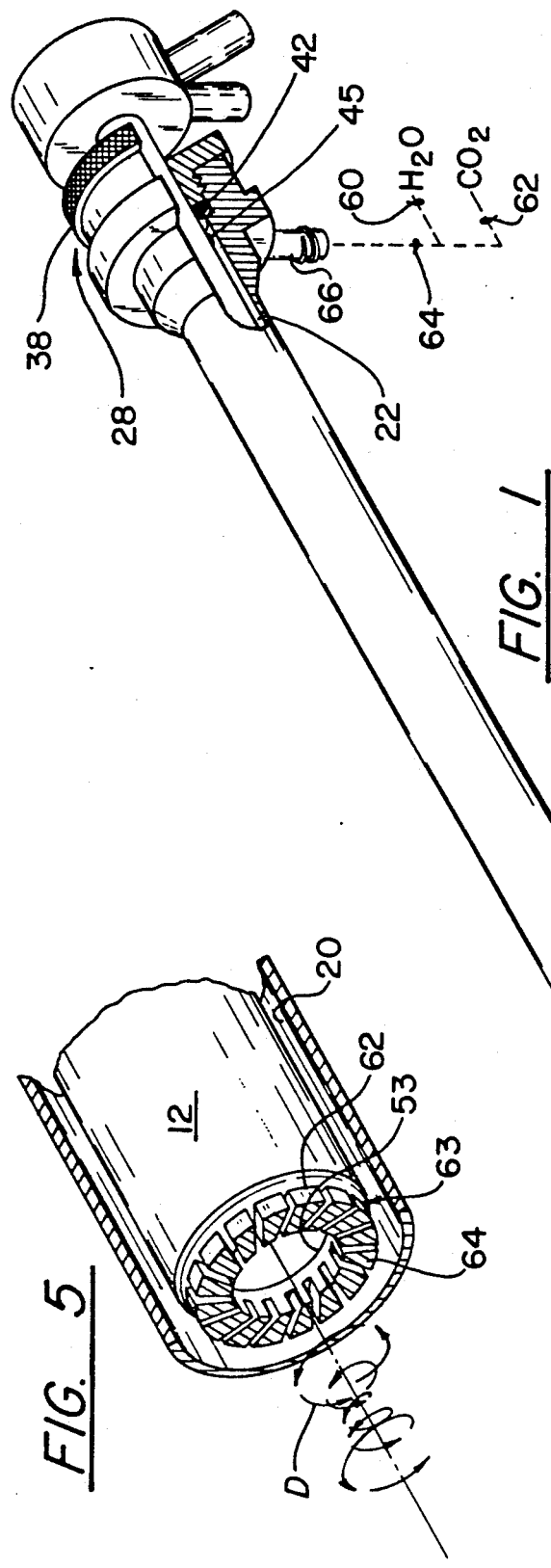
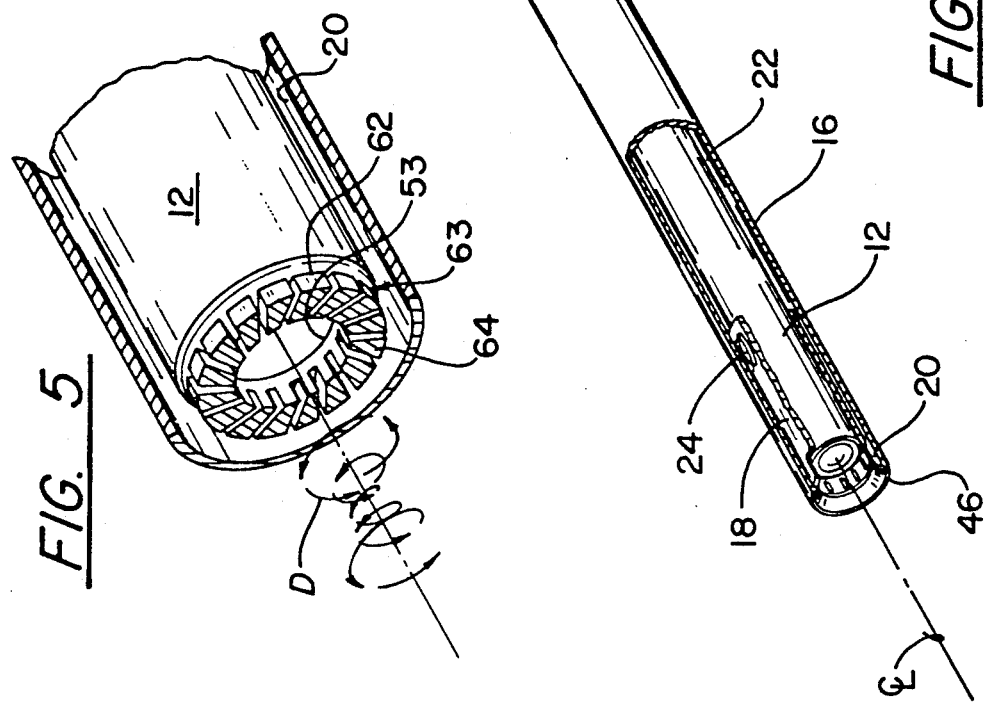

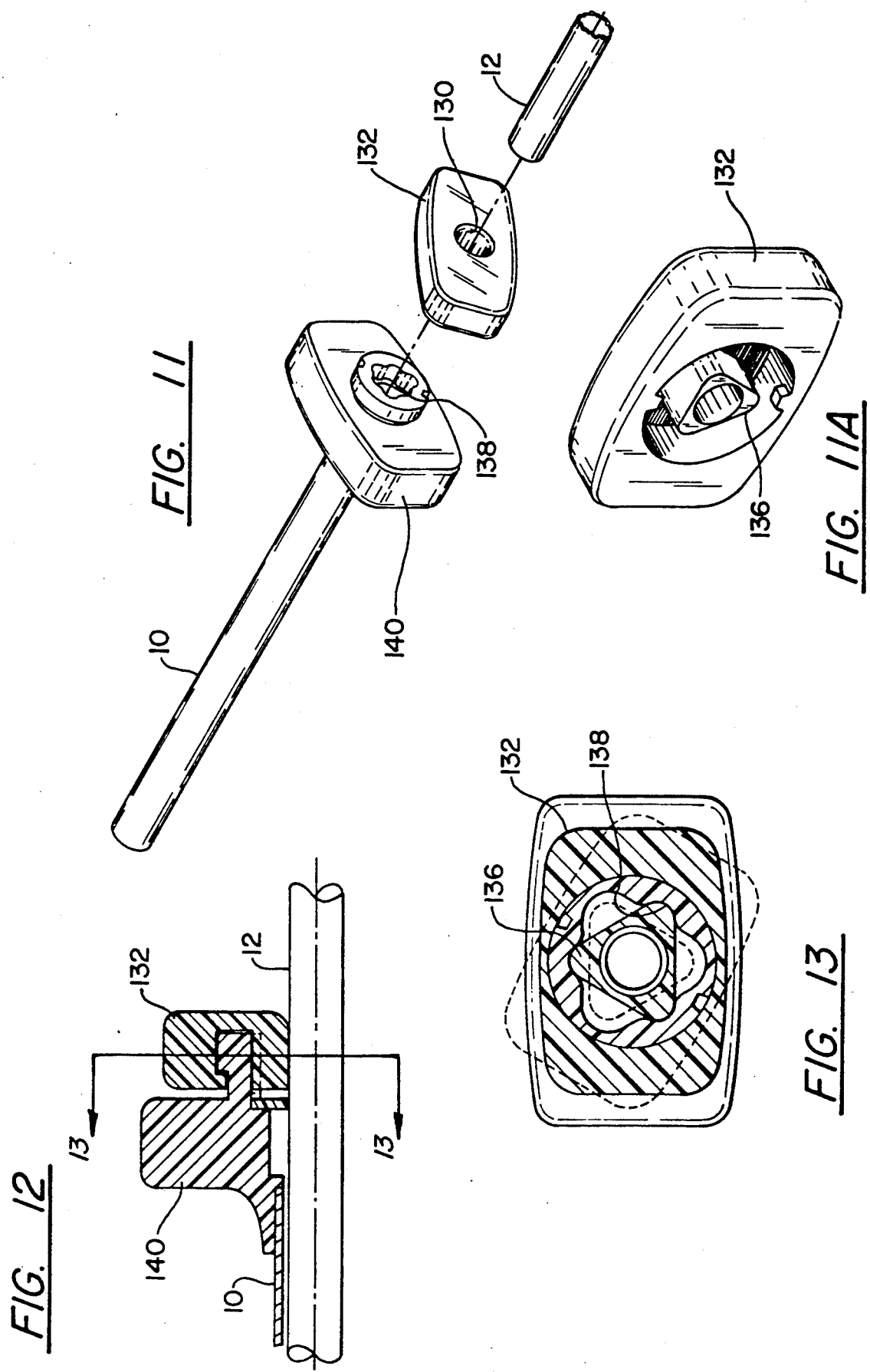

LENS CLEANING MEANS FOR INVASIVE VIEWING MEDICAL INSTRUMENTS

TECHNICAL FIELD

This invention relates to biological viewing instruments that include a lens used for video cameras or the like for internal viewing of the body and particularly to means for cleansing and shielding the lens.

BACKGROUND ART

There are a number of lens cleaning devices that are described in the prior art that are used on endoscopes, resectoscope, fiberscope catheterization devices and the like that provide for means for cleansing the lens. For example U.S. Pat. No. 4,770,163 granted to Ono et al on Sep. 13, 1988 and U.S. Pat. No. 4,576,146 granted to Kawazoe et al on Mar. 18, 1986 disclose an apparatus for viewing blood vessels and the like by continuously flowing saline fluid through a passage formed in the endoscope at a flow rate that approximates the blood flow rate. Of particular interest is the lens cleaning means disclosed in these patents which show a pair of passageways that include outlets that flow the saline solution in front of the lens. The outlets serve to orient the flow so that the flow discharging from the outlets of each of these passageways oppose each other and hence, according to this patent, the interaction of the opposing fluids keeps the lens clean.

Also of interest as disclosed in the U.S. Pat. No. 4,576,146, supra, is the spiral passageway for injecting the saline solution with a spiral flow to displace the opaque liquid in the region of observation.

U.S. Pat. No. 4,690,140 granted to Mecca on Sep. 1, 1987 discloses an endoscopic tube with a passageway to route clear liquid to circulate around the endoscopic tube. Again this is another attempt to keep the lens clean.

U.S. Pat. No. 4,633,855 granted to Baba on Jan. 6, 1987 also discloses an endoscope that includes a tube mounted internally within the endoscope where the end at the distal end is bent approximately 90 degrees and directed toward the lens so as to blow air or water adjacent the observation window in order to keep it clean.

While these lens cleaning means may be satisfactory in certain biological procedures, they are not satisfactory for others. In the application of video-surgery in laporoscopic and arthroscopic procedures, for example, we have found that creating a film of cleaning fluid to form over the lens surface is a far more satisfactory method of keeping the lens clean or defogged, if it fogs up. In certain instances. injection of the fluid, which may be either water or carbon dioxide, intermittently as needed has proven to be a satisfactory method of keeping the lens clean and defogged.

This invention employs a radial cavity with either partial or full circumferential flow directed over the surface of the lens or lens cover. In other embodiments this invention contemplates incorporating a vortex generator circumferentially mounted around the lens. This invention also contemplates incorporating a judiciously mounted fluid conveying passage integrated within the sheath surrounding the flexible types of medical instruments.

SUMMARY OF THE INVENTION

An object of this invention is to provide for a biological viewing instrument improved means for cleaning and/or shielding the lens.

A feature of this invention is to provide a sheath surrounding the tube supporting the fibre optics that provide light and transmits the image to the camera (video or other types) used in video surgery that includes a passage for flowing fluid to the discharge end that includes a radial channel with partial or full fluid flow capability formed in a cuff downstream of the lens and means to redirect the flow and coalesce the fluid and direct a film of fluid adjacent the surface and toward the center of the lens.

Another feature of this invention is to provide at the distal end of a concentric sheath surrounding the medical tubular instrument used for biological observations a vortex generator circumferentially disposed relative to the lens of the instrument.

Another feature of this invention is to provide for a flexible medical instrument used for biological observation or video surgery a sheath fabricated from flexible material concentrically mounted relative to the instrument with a helical passage formed integrally with the sheath defining a channel for the passage of fluid.

A feature of this invention is to provide a sheath and means for cleaning and/or shielding the lens of a biological observation instrument that is characterized as being capable of being adapted to existing instruments or being fabricated integrally with these types of instruments. A still further feature of this invention is that the structure of this invention can be sterilized via an autoclave method. The instrument can also be used to irrigate an adjacent area in the body by flowing fluid through the lens cleaning instrument to obtain a clearer view of the surrounding area.

Another feature of this invention is the incorporation of a two-part handle having the inner part connected to the lens cleaning apparatus and the upper part being rotatable relative to the lower part and each part having a camming arrangement for locking the lens carrying tube by a slight turn of the one handle relative to the other.

The foregoing and other features and advantages of the present invention will become more apparent from the following description and accompanying drawings.

BRIEF DESCRIPTION OF THE DRAWINGS

FIG. 1 is a perspective view partly in section illustrating the invention adapted to fit a borescope, FIG. 3 is an enlarged sectional view of the end cap for securing the invention to an existing borescope, FIG. 5 is an enlarged view illustrating a vortex generator attachment, FIG. 8A is a partial view in section illustrating the rib portion for defining the helical flow path.

FIG. 11A is a view in perspective of the bottom of a component of the handle of this invention;

FIG. 11 is an exploded view in perspective illustrating the two-part locking handle, and FIG. 12 is a partial view partly in section illustrating the two piece locking handle.

FIG. 13 is a sectional view, partly in phantom, taken along lines 13—13 illustrating the handle in the unlocked position.

BEST MODE FOR CARRYING OUT THE INVENTION

While in its preferred embodiment this invention is contemplated for use in video surgery, as for example for performing appendectomies, removal of gall bladders, removal of cancerous prostrate glands, and the like and for biological observation, it is to be understood that this invention has application in any environment where a lens is inserted into a cavity and ready access to cleanse the lens is not available. In a typical medical operation using video cameras the portion of the body to be observed is invaded by a Trocar which incises a small cylindrical hole through the body skin and tissue and is withdrawn leaving a hollow plastic tube in place. A tubular instrument (hereinafter referred to as a borescope) carries bundles of fiber optics which serves to transmit high intensity light beams to illuminate the area being treated and carries images back to the TV camera to view the sighted area. This invention is only concerned with the lens that is located at the distal end of the borescope an particularly to means that cleanse and shield it.

While the invention contemplates incorporating cleansing and shielding means to existing borescopes it is also within the scope of this invention to fabricate the borescope integrally with this invention.

Figure 2:
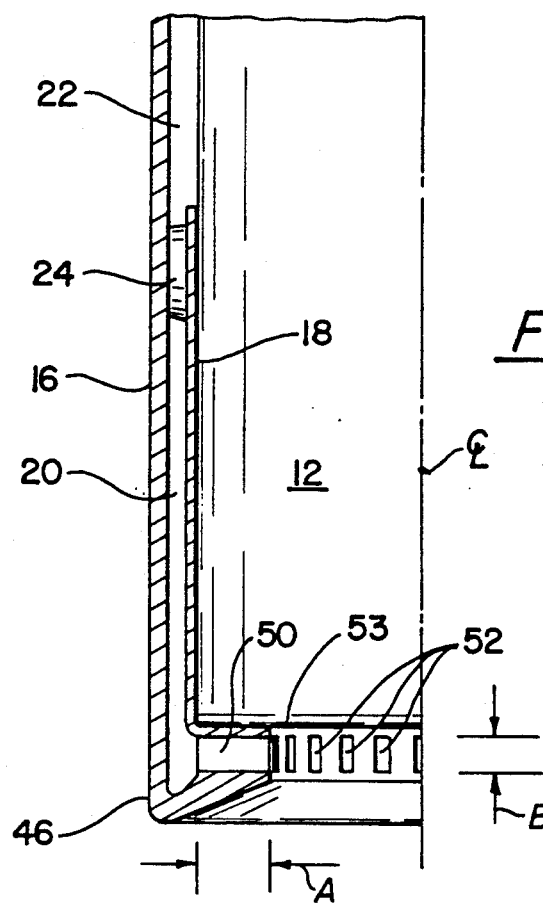
FIG. 2 is an enlarged partial view in section showing details of the lens cleaning passages of the embodiment shown in FIG. 1.

To best understand this invention reference is now made to FIGS. 1-3 depicting a hollow cylindrical tube 10 adapted to concentrically fit over the borescope 12. The diameter is selected to provide an annular space between the outside diameter of the borescope 12 and the inner diameter of the tube 10 having specific dimensions for the passage of sufficient fluid necessary for lens cleansing and shielding.

In the preferred embodiment the bottom or distal end is formed in two cylindrical pieces concentrically mounted relative to each other. The outer piece or sheath 16 extends the entire length of the tube and the inner piece is a short tube 18 mounted at the distal end and extends axially a short distance up the sheath 16. The diameter of the inner short tube 18 forms a snug fit with the outer surface of the borescope 12 and is slightly spaced to form the annular passage 20 that is in fluid communication with the annular passage 22 defined by the sheath 16. A plurality of spacers 24 are circumferentially spaced and extend between short tube 18 and the inner surface of sheath 16 and are suitably bonded thereto and serve to keep the two tubes in concentric alignment.

A retention nut and gland combination 28 threadably engages threads 30 formed on the inner diameter of sheath 16 at the proximal end and serves to secure and seal the sheath to the borescope. The outer circumference at the end of nut 38 may be knurled in order to manually torque the nut to the sheath. Sealing means, say 0-ring seal 42, seals off the end to the passage 22.

Fluid is supplied to passage 22 through opening 45 formed in the sheath 16 and fluid such as water or carbon dioxide from a source (not shown) is regulated by suitable and commercially available valves, such as trumpet valves that are normally biased close and merely require depressing the valve stem to open, similar to those used in musical instruments.

According to this invention, the fluid in passages 22 and 20 is directed to a cuff 46 extending from and formed a part of sheath 16 that protrudes beyond the distal end of borescope 12. The passage 20 in cuff 46 includes a curved or flat bottom that serves to change the direction of the flow in passage 20. By virtue of the momentum of the flow the stream is directed to flow in the transverse passages 50 and discharge through the annular spaced outlets 52 and is directed toward the central axis of the lens. The stream of fluid is made to coalesce to form a film or sheet of fluid to flow over the outer surface of the lens cover 53. The dimensions of passage 50 and annular outlet are critical in that they are sized to give direction and coalesce the flow into a film which serves to clean the lens cover or lens directly if no cover is utilized. The dimensions of the length of the transverse passage 50 depicted by arrow A and the height of transverse passage 50 depicted by arrow B are critical and are selected so that the size of dimension A is substantially larger than the size of dimension B. In actual tests satisfactory results were obtained when the dimension of A was twice the dimension of B.

In operation suitable valves 60 or 62 (schematically shown) are activated to flow fluid through the line 64 coupled to fitting 66 which admits the fluid to annular passages 22 and 20 via the opening 45. The flow proceeds to the cuff 46 where it is guided by the bottom surface 47 and is forced to redirect the flow into the plurality of circumferential spaced passages 50. The flow discharging from the passages 50 are directed toward the central axes C of the borescope 12. The fluid may be preheated in order to accommodate the defogging feature of this invention.

Another advantage of the cuff 46 is that by virtue of the fact that it extends axially beyond the lens cover it serves to shield the lens from being in direct contact with body tissue and in fact creates a space between the outer edge of the cuff and the surface of the lens which allows the intensive light being transmitted by the fiber optics to diffuse in this space and maintain visibility.

As will be appreciated from the foregoing that the outlet 52 is in a form of an annulus and is in proximity to the lens and in fact circumscribes the lens. This serves to attract, by capillar attraction, any liquid droplets that should remain on the lens after the liquid has been turned off. The attraction of the droplets is by a adhesion effect which has a tendency of drawing the liquid back toward the annulus and as a consequence the droplets are removed from the lens and thereby avoiding any distortion of the image being transmitted to the camera.

Figure 4:
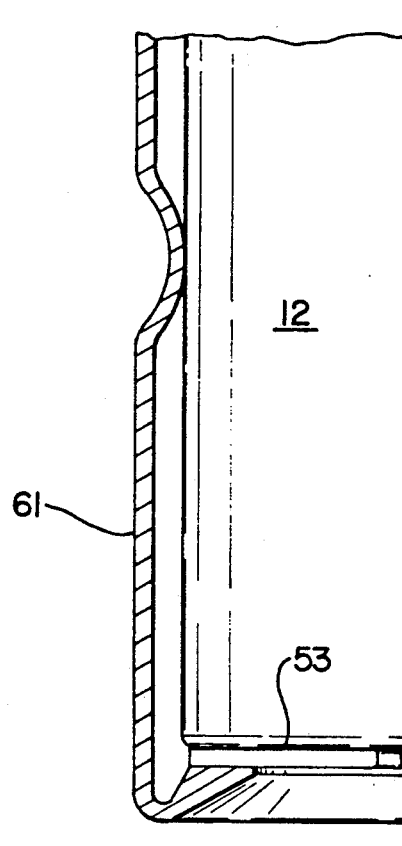
FIG. 4 is an enlarged partial sectional view illustrating another embodiment of this invention.

FIG. 4 depicts another embodiment of this invention where the number of outlets 52 are significantly reduced so that the span of the circumferential dimension is increased, simplifying the fabrication of the invention.

Also the other sheath 61 is crimped at some distance up from the bottom end to form a dimple that bears against the outer circumferential surface of borescope 12 to keep the outer tube in concentric alignment. This replaces the spacers depicted in FIG. 1 to simplify the manufacture of the sheath.

It is contemplated within the scope of this invention that instead of having the fluid discharge from the outlets 52 in a stream that is parallel or generally parallel to the lens cover, a vortex generator will be mounted at the outlet to impart a swirling motion to the fluid to in effect create vortices in front of the lens which will serve to not only clean the lens or its surface but also prevent loose tissue or other opaque substances from impinging on the lens. A suitable vortex generator generally indicated by reference numeral 63 is shown in FIG. 5. Generally the vortex generator is a ring-like member 62 that carries a pluralities of upstanding vanes 64 spaced around the circumference. Vanes 64 serve to impart a swirl to the fluid passing therebetween so that the fluid discharging from the vane defines a helical path depicted by the arrow D.

As is apparent from the foregoing the cleaning fluid that exits the channels defined between adjacent vanes 64 flows tangentially toward the center line C, across the lens and with a spiral motion the fluid then travels in an axial/radial direction outwardly over the face of cuff 46 and as a secondary cleaning function serves to prevent opaque fluids present in the body from migrating from the cuff to the lens. The swirling fluid serves to not only keep the lens clean or defogged but also creates a shield to protect the lens from loose matter in the area being viewed.

The components of the lens cleaning system can be fabricated from suitable and well known metallic or non-metallic materials.

Figure 6:
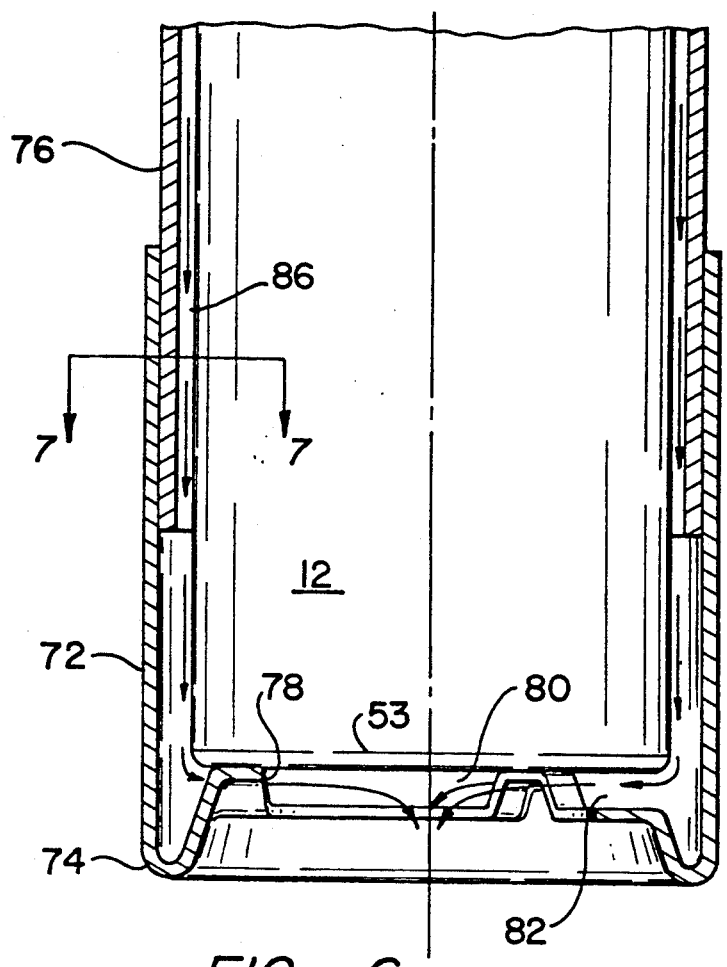
FIG. 6 is an enlarged partial sectional view illustrating another embodiment of this invention.
Figure 7:
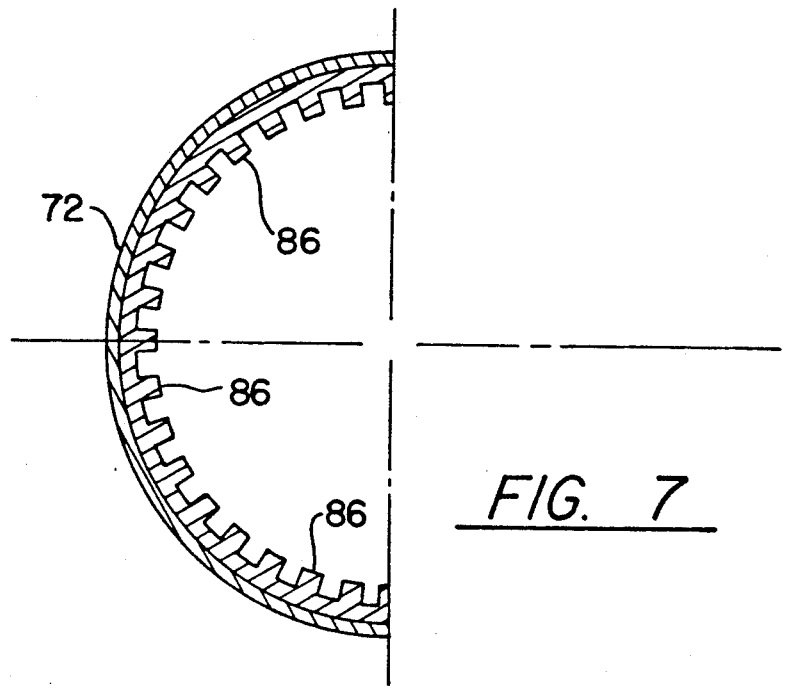
FIG. 7 is a partial view in section taken along lines 7—7 of FIG. 6.

FIGS. 6 and 7 exemplifies another embodiment of this invention where the short tube 72 defining cuff portion 74 is fabricated from sheet metal stock and is attached to the end of sheath 76 (similar to sheath 16 depicted in FIG. 1). The bottom end is crimped to define dimple 78. The lens cover 53 bears against the dimple 78 when installed and defines the space 80 to allow the flow discharging from the annular discharge 82 to flow over the surface of the lens. Similar to the embodiment depicted in FIG. 1, the cuff 74 serves to change the direction of the flow so that the flow passes beyond the lower extremity of the distal end of borescope 12 and is redirected to the outlet discharge end before being discharge adjacent the surface of the lens. In this embodiment of FIGS. 6 and 7 the tube 76 is held in concentric relationship with the borescope 12 by the scallops 86 formed on the inner diameter of tube 76.

Figure 8:
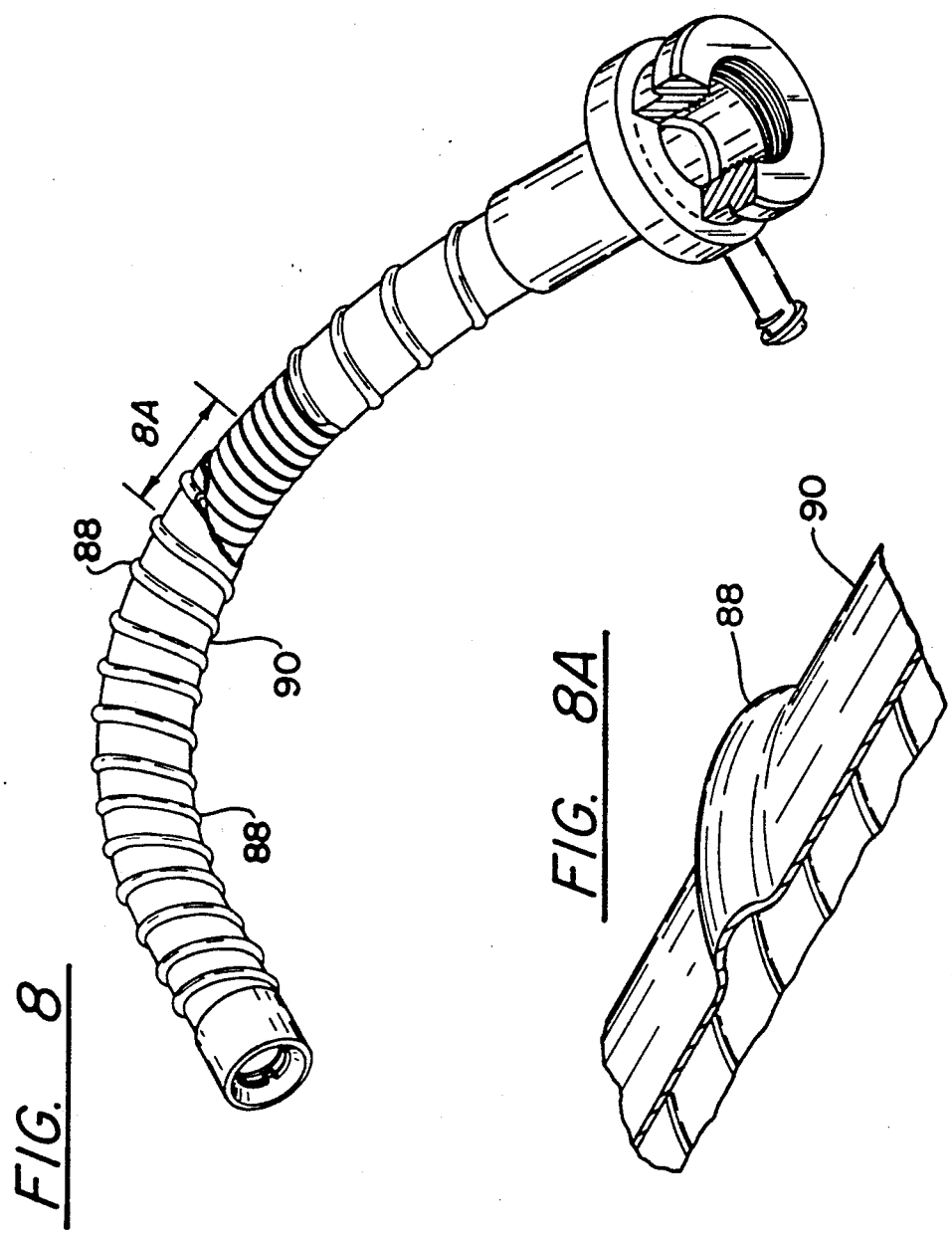
FIG. 8 is a view in perspective illustrating another embodiment of this invention when applied to a flexible borescope.

FIGS. 8 and 8A exemplifies this invention when the borescope is formed from a flexible tube. In this embodiment a helical formed channel 88 is formed in the flexible tube 90 which may be fabricated similar to BX metal cable to define the passage for flowing the fluid from the inlet to the discharge end. The cuff portion which can be identical to the versions shown in FIGS. 1, 4, and 6 is secured to the end of the flexible tube 90. As seen in FIG. 8A the rib 88 defines a flexible helical channel to the borescope outside diameter for delivering the fluid from the proximal end to the distal end of the lens cleaning tubular member.

Figure 9:
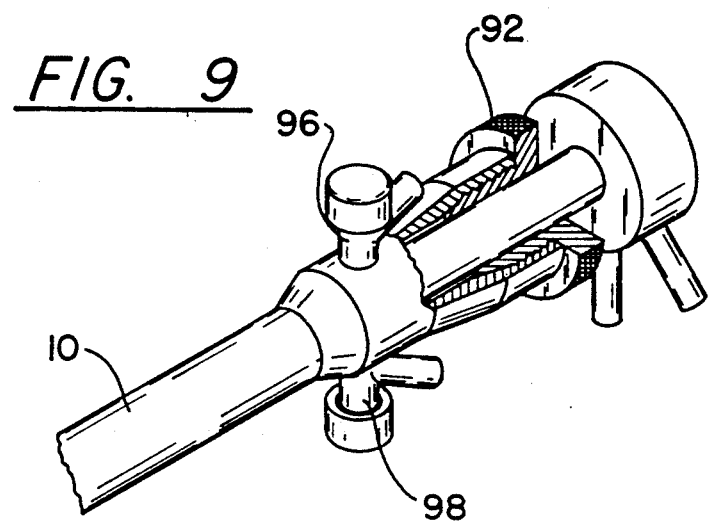
FIG. 9 is a partial view in perspective and partly in section illustrating a version of this invention employing a valving arrangement for controlling the cleansing and/or shielding fluids.
Figure 10:
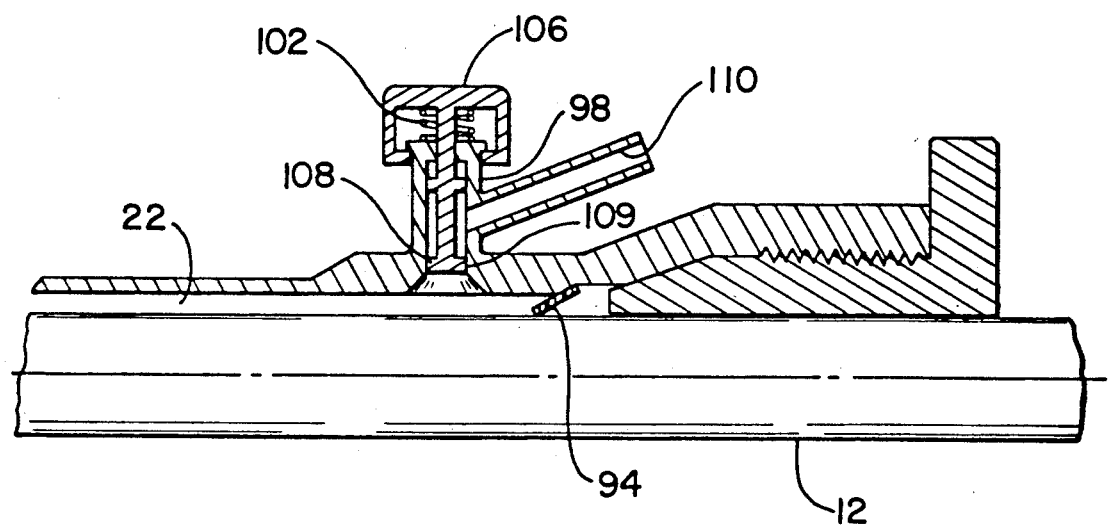
FIG. 10 is a partial view in section showing the details of the embodiment of FIG. 9.

FIGS. 9 and 10 illustrate optional attachment means and trumpet valve means that can be employed with this invention. In this embodiment the borescope 12 is inserted in the tube 10 and held in place by end cap and bolt 92 threaded to the end of tube 10. A packing or gland illustrated by reference numeral 94 seals the end of the borescope 12. Suitable trumpet valves 96 and 98 serve to admit the fluid desired. The trumpet valve as shown in FIG. 10 consists of a plunger 100 that is spring biased by coil spring 102 in the upward direction. Depressing button 106 positions valve element 108 away from seat 109 placing passage 110 in fluid communication with passage 22.

In accordance with this invention and as can be seen in FIG. 11 and FIG. 12 a two-piece handle is provided to conveniently lock the tubular member 10 to the borescope 12. The borescope 12 is inserted in the central passage 130 and extends throughout the distal end. The upper handle 132 carries an elongated triangular shaped cam element 136 that extends into the aperture 138 formed in lower handle 140. Aperature 138 is configured to define detents that have a smaller diameter area than the diameter area of the aperature 138. Hence, by rotating the upper handle 132 relative to the lower handle 140, which is held in place by the operator with the use of his other hand, the apex of the triangular shaped cam 136 fits into the smaller diameter area detents and the material of cam 136 is sufficiently flexible and resilient to frictionally engage the outer diameter of the borescope 12 and lock it into place.

As will be appreciated by those skilled in this art another use of the lens cleansing apparatus is the ability to irrigate the surrounding area by injecting a stream of fluid in the area where the surgeon requires a better or clearer view. To accomplish irrigation the operator merely depresses the trumpet valve to allow a stream of fluid to be injected in the surrounding area and leaves the valve in the operative mode until the area is visible. It is contemplated within the scope of this invention that the trumpet valve can include suitable means to hold the valve in the operative position.

Although this invention has been shown and described with respect to detailed embodiments thereof, it will be appreciated and understood by those skilled in the art that various changes in form and detail thereof may be made without departing from the spirit and scope of the claimed invention.

What is claimed:

1. Apparatus for cleansing the lens of a viewing camera used in biological observation by penetration into the cavity of living beings, the camera having an elongated tube housing fibre optics for producing a lighted area from a light source and a image relay for a television camera, a lens at the distal end of said elongated tube, the improvement comprising:

a tubular member concentrically mounted around said elongated tube and being spaced therefrom to form a longitudinal passageway, a cuff portion extending beyond the distal end of said elongated tube to reduce lens contact with body parts to inhibit opaque fluids from obscuring visibility, said cuff portion including fluid passage means in fluid communication with said longitudinal passageway and being laterally disposed relative thereto and defining at least one discharge port at the end of said fluid passage means for directing fluid in a lateral direction, said cuff portion including a bottom wall surface extending below said fluid passage means for redirecting the flow of fluid in said longitudinal passageway and to flow into said fluid passage means to discharge from said discharge port and flow laterally in a direction to scrub the surface of the lens mounted at the distal end of said elongated tube, said discharge port being sized to coalesce and direct the flow of fluid to form a sheet of fluid, and means for admitting fluid into said longitudinal passageway whereby the flow of fluid formed into a sheet is directed over the lens on demand of the operator.

2. Apparatus as claimed in claim 1 wherein said fluid passage means includes a predetermined length and said discharge port includes a length and height and the dimension of said predetermined length of said fluid passage means is larger than said height said discharge port.

3. Apparatus as claimed in claim 2 wherein said predetermined length of said fluid passage means is substantially equal to two times the dimension of said height of said discharge port.

4. Apparatus as claimed in claim 1 wherein said longitudinal passageway is annular.

5. Apparatus as claimed in claim 1 including a circumferential rim defined by said cuff disposed relative to the edge of said discharge port for adhering through capillary retraction droplets of fluid that remain on said rim in proximity to said lens after the flow of fluid is discontinued and when the fluid is a liquid.

6. Apparatus as claimed in claim 1 including means for generating a vortex of said fluid disposed at the end of said discharge port.

7. Apparatus as claimed in claim 6 wherein said means for generating a vortex includes a plurality of spaced vanes circumferentially spaced about an axis that is disposed coaxially relative to the longitudinal axis of said lens.

8. Apparatus as claimed in claim 5 wherein the internal diameter of said tubular member is threaded, an end cap including a threaded shank portion threadably supported to said internal threads for placing said elongated tube and said tubular member in locking relationship.

9. Apparatus as claimed in claim 8 including sealing means disposed between said tubular member and said elongated tube at the lower end of said shank.

10. Apparatus as claimed in claim 8 including normally closed valve means disposed between said cap and said proximal end of said elongated tube operable externally of the body for opening said valve means and flowing fluid into said longitudinal passageway.

11. Apparatus for cleansing the lens of a viewing camera used in biological observation by penetration into the cavity of living beings, the camera having a flexible elongated tube housing fiber optics for producing a lighted area from a light source and a image relay for a television camera the improvement comprising:

a flexible tubular member concentrically mounted around said elongated tube having a helical extending rib portion defining a helical passage, a cuff portion extending beyond the distal end of said elongated tube including an annular passage and fluid passage means in fluid communication with said helical passage and defining at least one discharge port at the end of said fluid passage means, said annular passage of said cuff portion including a bottom wall surface for redirecting the flow of fluid in said fluid passage means to discharge from said discharge port and flow laterally in a direction to scrub the surface of the lens mounted at the distal end of said elongated tube, said fluid passage means and said discharge port being sized to coalesce and direct the flow of fluid to form a sheet of fluid, and means for admitting fluid into said helical passage whereby the flow of fluid formed into a sheet is directed over the lens on demand of the operator.

12. Apparatus for cleansing the lens of a viewing camera used in biological observation by penetration into the cavity of living beings, the camera having an elongated tube housing fibre optics for producing a lighted area from a light source and a image relay for a television camera, a lens at the distal end of said elongated tube, the improvement comprising:

a tubular member concentrically mounted around said elongated tube and being spaced therefrom to form a longitudinal passageway, means for generating a vortex of said fluid disposed at the end of said longitudinal passageway, said means for generating a vortex including a plurality of vanes circumferentially spaced about an axis that is disposed coaxially relative to the longitudinal axis of said lens, and means for admitting fluid into said longitudinal passageway whereby the flow of fluid formed into a vortex is directed over the lens on demand of the operator.

* * * * *